United States Patent
Lee et al.

(10) Patent No.: US 7,075,070 B2
(45) Date of Patent: Jul. 11, 2006

(54) SINGLE DEVICE FOR ION MOBILITY AND ION TRAP MASS SPECTROMETRY

(75) Inventors: Edgar D. Lee, Highland, UT (US); Alan L. Rockwood, Provo, UT (US); Milton L. Lee, Pleasant Grove, UT (US); Samuel E. Tolley, Springville, UT (US)

(73) Assignee: Brigham Young University, Provo, UT (US)

( * ) Notice: Subject to any disclaimer, the term of this patent is extended or adjusted under 35 U.S.C. 154(b) by 67 days.

(21) Appl. No.: 10/873,752

(22) Filed: Jun. 21, 2004

(65) Prior Publication Data

US 2005/0029445 A1 Feb. 10, 2005

Related U.S. Application Data

(60) Provisional application No. 60/480,052, filed on Jun. 20, 2003.

(51) Int. Cl.
*B01D 59/44* (2006.01)
*H01J 49/00* (2006.01)

(52) U.S. Cl. ............. 250/294; 250/281; 250/282
(58) Field of Classification Search ........ 250/294, 250/281, 282
See application file for complete search history.

(56) References Cited

U.S. PATENT DOCUMENTS

| 5,942,752 | A | 8/1999 | Wang |
| 6,124,592 | A * | 9/2000 | Spangler ............... 250/287 |
| 6,504,149 | B1 | 1/2003 | Guevremont et al. |
| 6,744,043 | B1 * | 6/2004 | Loboda ............... 250/287 |
| 6,770,875 | B1 * | 8/2004 | Guevremont et al. ....... 250/288 |
| 6,787,765 | B1 | 9/2004 | Guevremont et al. |
| 6,815,669 | B1 | 11/2004 | Miller et al. |
| 6,831,271 | B1 | 12/2004 | Guevremont et al. |
| 2003/0047681 | A1 | 3/2003 | Guevremont et al. |
| 2003/0136680 | A1 | 7/2003 | Benner et al. |

FOREIGN PATENT DOCUMENTS

EP   0 878 828 A1   11/1998

* cited by examiner

*Primary Examiner*—John R. Lee
*Assistant Examiner*—Jennifer Yantorno
(74) *Attorney, Agent, or Firm*—Morriss O'Bryant Compagni (57) ABSTRACT

A single set of electrodes, wherein different electrical potentials are applied to the single set of electrodes at different times in order to perform both ion mobility-based spectrometry and mass spectrometry (MS) on a sample of ions, wherein the ions are processed by performing ion mobility-based spectrometry and mass spectrometry in any sequence, any number of times, and as isolated or superposed procedures in order to trap, separate, fragment, and/or analyze charged particles and charged particles derived from atoms, molecules, particles, sub-atomic particles and ions.

40 Claims, 10 Drawing Sheets

SINGLE DEVICE FOR ION MOBILITY AND ION TRAP MASS SPECTROMETRY

CROSS REFERENCE TO RELATED APPLICATIONS

This document claims priority to, and incorporated by reference all of the subject matter included in the provisional patent application Ser. No. 60/480,052 and filed on Jun. 20, 2003.

BACKGROUND OF THE INVENTION

1. Field of the Invention

This invention relates generally to storage, separation and analysis of ions according to ion mobilities and mass-to-charge ratios, in the same device, of charged particles and charged particles derived from atoms, molecules, particles, sub-atomic particles and ions. More specifically, the present invention is a single device that enables ion trap mass spectrometry (ITMS) and ion mobility spectrometry, such as high-field asymmetric ion mobility spectrometry or FAIMS, differential mobility, cross-flow ion mobility spectrometry to be performed in a single device, and in any sequence, to thereby perform both types of separation wherein at least two uniquely different chemical-specific identifiers can be obtained to provide identification of the ions.

2. Description of the Related Art

The trapping, separation, ejection and analysis of ions according to ion mobilities and mass-to-charge ratios have always been performed in two distinct devices that perform the operations of ion mobility spectrometry and mass spectrometry. Thus, if it is desired to sequentially analyze the sample using both procedures, it has been necessary to provide separate devices that are in some manner connected in series so that ions can travel from one device to the other.

There are at least several obvious disadvantages to such a serial configuration of devices. First, the operations that can be performed are limited to the specific order in which the devices have been disposed. Second, two distinct devices have always been required, thereby increasing complexity, size and cost of the overall system. Third, there is typically some loss of ions as they travel from one device to another for the different operations to be performed.

To understand the advantages of the present invention and understand how they can be combined in a single device, it is useful to briefly examine the state of the art of both mass spectrometry and ion mobility spectrometry.

Beginning with mass spectrometry, it is a popular instrumental method for analyzing ions. In mass spectrometry, ions are separated according to their mass-to-charge ratios in various fields, such as magnetic, electric, and quadrupole. One type of quadrupole mass spectrometer is an ion trap. Several variations of ion trap mass spectrometers have been developed for analyzing ions. These devices include hyperbolic configurations, as well as Paul, dynamic Penning, and dynamic Kingdon traps. In all of these devices, ions are collected and held in a trap by an oscillating electric field. Changes in the properties of the oscillating electric field, such as amplitude, frequency, superposition of a DC field and other methods can be used to cause the ions to be selectively ejected from the trap to a detector according to the mass-to-charge ratios of the ions.

It is noted that one particular advantage of ion trap mass spectrometers is that these devices typically do not require as high a vacuum within which to operate as other types of mass spectrometers. In fact, the performance of the ion trap mass spectrometer can be improved due to collisional dampening effects from the background gas that is present. Ion trap mass spectrometers typically operate best at pressures in the mTorr range.

The other relevant method of ion analysis is ion mobility spectrometry. Ion mobility spectrometry is becoming increasingly important as an instrumental analytical chemistry technique for separating ions that are created from charged particles and charged particles derived from atoms, molecules, particles, sub-atomic particles and ions.

The basic principle of ion mobility spectrometry is that ions in a gas that are exposed to an electric field travel along the electric field lines at a velocity that is a function of the ion mobility constant K, and the electric field intensity E.

Conventionally, high-field asymmetric ion mobility spectrometry (FAIMS) is a form of ion mobility spectrometry that separates ions based on the combination of their low field and their high field ion mobilities. At a constant gas velocity, the dependence of the ion mobility coefficient is defined by Equation 1:

$$K(E) = K_0[1 + \alpha(E)]$$

where $K^0 = K(E)$ at zero electric field and $\alpha(E)$ accounts for the dependence of the mobility coefficient on E at a constant gas density.

If an asymmetric periodic electric field E(t) is applied to a mixture of ions in a gas with certain conditions, an asymmetric waveform is obtained where $T = t_1 + t_2$, where T is the field changing period. The effect of this field is that ions will oscillate in the gas with a period T. The velocity of each ion during $t_1$ and $t_2$ depends on the amplitudes of $E_{max}$ and $E_{min}$, respectively, and the magnitude of $\alpha(E)$. As a result, the ions will be displaced along the field lines when their $\alpha(E)$ values are different.

When discussing FAIMS, it is useful to examine some common configurations of a device that can perform this type of ion mobility spectrometry. Consider two electrodes that are defined as either two concentric tubes or plates. The high electric field is applied for a short time, and then the low electric field is applied for a longer duration, with the average applied electric field being balanced. The non-linearity of the FAIMS system is generally attributed to the different cross-sectional areas of the ions that are drifting through the tube or between the plates. Accordingly, the method takes advantage of the different mobilities of ions in a high electric field as compared to a low electric field.

As previously mentioned, another way of describing FAIMS is to say that the separation of ions is based on the nonlinear dependence of the mobility constant with respect to the electric field intensity. The change in mobility at high electric field values appears to reflect the size of the ion, its interaction with the buffer gas, and the structural rigidity of the ion. Thus, the combination of their low field and their high field ion mobilities is used to characterize the ions in FAIMS.

It would be an advantage over the prior art to provide a new system that combines, in a single device, the techniques of ion mobility-based measurement with mass spectrometry, to thereby take advantage of the benefits that can be derived from combining the hardware required to perform both of these procedures, eliminating the step of transporting ions from one device to another, and allowing these procedures to be performed in any desired sequence, and any number of times.

BRIEF SUMMARY OF THE INVENTION

It is an object of the present invention to provide a system that combines the ability to perform both ion mobility-based measurement and mass spectrometry (MS) in the same device.

In a preferred embodiment, the present invention is single set of electrodes, wherein different electrical potentials are applied to the single set of electrodes at different times in order to perform both ion mobility-based spectrometry and mass spectrometry on a sample of ions, wherein the ions are processed by performing ion mobility-based spectrometry and mass spectrometry in any sequence, any number of times, and as isolated or superposed procedures in order to trap, separate and analyze charged particles and charged particles derived from atoms, molecules, particles, sub-atomic particles and ions.

In a first aspect of the invention, the electrical potential that can be applied to various electrodes is modifiable so that the system can perform ion mobility-based, MS or a superposed operation of both procedures.

In a second aspect of the invention, an ion fragmentation step can be inserted between any of the ion mobility-based or MS procedures, or where the procedures are superposed upon each other.

In a third aspect of the invention, the system can be made small and portable for handheld operation by using the same system for both ion mobility-based and MS procedures.

In a fourth aspect of the invention, the system can be modified to enable cross-flow ion mobility analysis.

These and other objects, features, advantages and alternative aspects of the present invention will become apparent to those skilled in the art from a consideration of the following detailed description taken in combination with the accompanying drawings.

DETAILED DESCRIPTION OF THE INVENTION

Reference will now be made to the drawings in which the various elements of the present invention will be given numerical designations and in which the invention will be discussed so as to enable one skilled in the art to make and use the invention. It is to be understood that the following description is only exemplary of the principles of the present invention, and should not be viewed as narrowing the claims which follow.

There are various embodiments of the invention that need to be described in order to fully disclose all of the advantages of the present invention. Accordingly, it should be understood that there is no single preferred embodiment, but rather various embodiments having different advantages. No assumptions should be implied as to the best embodiment from the order in which they are described.

It should also be understood that the present invention performs trapping, separation, and analysis of various particles including charged particles and charged particles derived from atoms, molecules, particles, sub-atomic particles and ions. For brevity, all of these particles are referred to throughout this document as ions.

In the simplest terms, the present invention combines the hardware and circuitry for performing the procedures of mass spectrometry (MS) and ion mobility-based spectrometry in a single device. More specifically, FAIMS is being used for the ion mobility-based spectrometry procedure. Both FAIMS and MS procedures can be performed with simple modifications to circuit paths to thereby modify electrical potentials being applied to electrodes within the single device as will be explained hereinafter.

Figure 1:
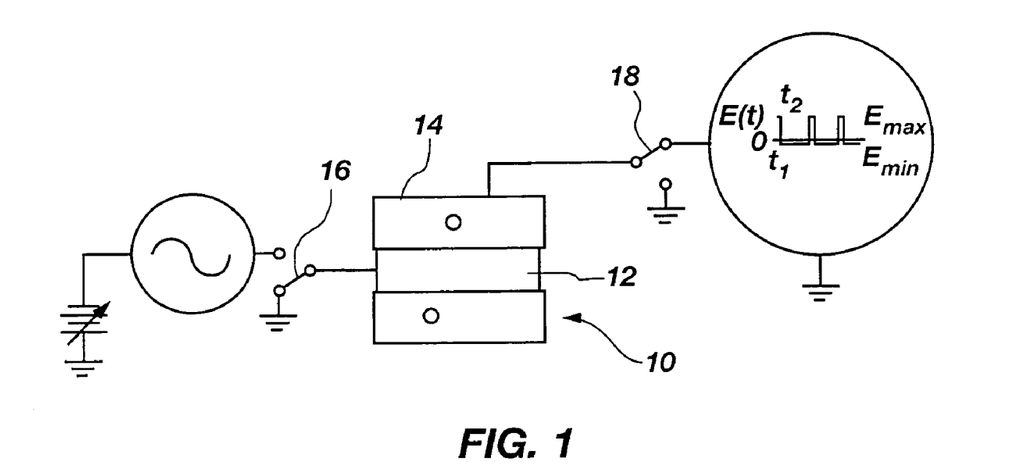
FIG. 1 is a profile view of a first embodiment that is operated in accordance with the principles of the present invention that is configured to perform in a FAIMS mode.

FIG. 1 is a profile view of a first embodiment that is made in accordance with the principles of the present invention. In this embodiment, the single device 10 that is able to perform both mass spectrometry and FAIMS is shown as a circular rod electrode 12 disposed coaxially with an outer cylindrical electrode 14.

In order to perform FAIMS, the circular rod electrode 12 is typically held at a constant potential or at ground, and an asymmetric FAIMS waveform is applied to the outer cylindrical electrode 14. It should be noted that wherever a constant potential or ground is being applied, a dynamic or constant common mode potential can be used.

During the FAIMS procedure, all of the ions oscillate back and forth between the inner circular rod electrode 12 and the outer cylindrical electrode 14. Only ions as determined by the combination of their low field and their high field ion mobilities are trapped in the single device 10. All other ions are lost to the circular rod electrode 12 and the outer cylindrical electrode 14.

The desired electrical potentials are applied to the electrodes 12 and 14 by way of the switches 16 and 18. Switch 16 is shown applying a ground potential to the inner circular rod electrode 12, and switch 18 is shown applying the FAIMS waveform. Accordingly, ions are selected according to ion mobility by applying the desired potentials to operate the single device in a FAIMS configuration.

Figure 2:
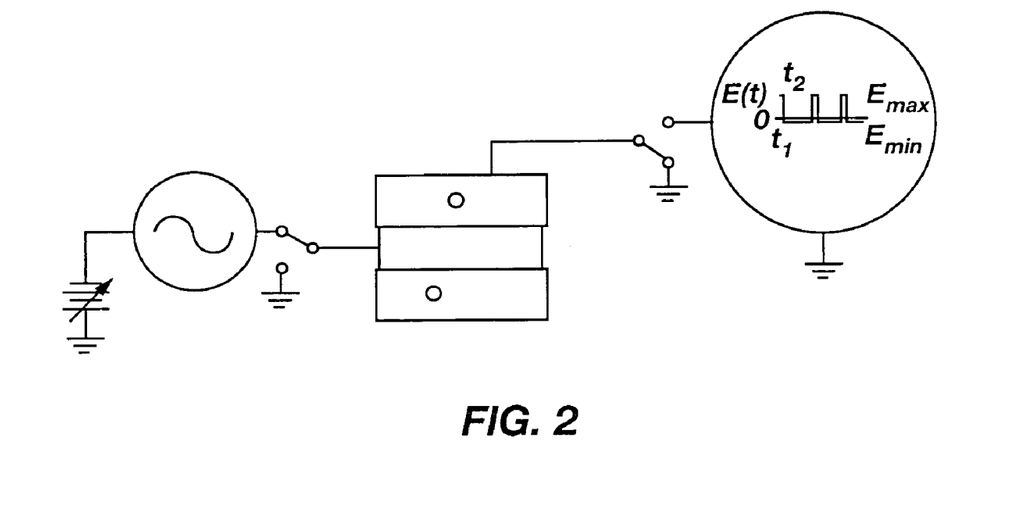
FIG. 2 is a profile view of the first embodiment that is altered to thereby perform in an MS mode.

Advantageously, the same single device 10 can be operated as shown in FIG. 2. FIG. 2 shows that switches 16 and 18 have been moved to their alternate positions. In these new alternate switch positions, an oscillating RF potential is applied to the inner circular rod electrode 12, and the outer cylindrical electrode 14 is held at a constant potential, which in this case is shown as being at ground. It is again noted that a dynamic common mode potential can be used. In this mode of operation, all ions in the single device 10 are first trapped, and then sequentially ejected from the trap according to their mass-to-charge ratios. Ejection is accomplished by changing the RF field by either modifying a superposed DC voltage, or by varying the amplitude, frequency or other aspect of the applied potentials.

It should be understood that any appropriate ionization techniques can be used to create the ions within the single device 10, or create the ions for delivery to the single device. The following is a list of some commonly used ionization techniques: electron impact, chemical ionization, fast ion or atom bombardment, field desorption, laser desorption, plasma desorption, thermospray, electrospray, photoionization, inductively coupled plasma, and any other method of ionization. This list should be considered as representative only, and is not intended to exclude other appropriate ionization systems that may also be used with the single device 10 of the present invention. For example, the ions can be created within the single device 10 itself as opposed to being delivered to it.

The single device 10 is first operated in a FAIMS mode to thereby select ions according to specific ion mobility, and then switched to the ITMS mode to determine the mass of the ions. By operating the single device 20 in this manner, at least two uniquely different chemical-specific identifiers can be obtained to provide identification of the ions.

What should now be apparent is that the single device 10 is very versatile in its modes of operation. For example, the single device 10 could first be operated in the ITMS mode, and then in the FAIMS mode. Furthermore, the single device 10 could also be operated to perform any number of FAIMS and ITMS procedures, and in any desired order. Thus the present invention enables any sequence of ITMS and FAIMS procedures to be performed, and to be performed any number of times.

Another advantage of the present invention is that the ITMS and FAIMS modes of operation are not the only procedures that can be performed using the single device 10. Therefore, the configuration of the single device 10 shown in FIGS. 1 and 2 may enable other operations to be performed. Furthermore, the configuration of the single device 10 can be altered and still perform the desired FAIMS and ITMS procedures, while allowing other different procedures to also be performed.

An example of a useful procedure that can be added to the FAIMS and ITMS procedures is that of ion fragmentation. It is often desirable to fragment an ion mobility-selected or mass-selected ion using collisionally induced dissociation, or any other means. For example, fragmentation can be performed by particle collision, surface induced fragmentation, photo induced fragmentation including visible, ultraviolet and infrared methods, electron beam, energetic ion beam, low energy electron attachment, and electron abstraction to name some.

Any other means of performing fragmentation that are possible using the single device 10 or other configurations, and known to those skilled in the art, should all be considered viable fragmentation methods that are included within the scope of the present invention.

Now that it is understood that the configuration of the single device may take other forms other than the one that is illustrated in FIGS. 1 and 2, it should be understood that the single device can also include a cross-flow ion mobility mode of operation.

A single device that is capable of performing FAIMS, ITMS, and cross-flow ion mobility analysis must be modified in order to include the features that make cross-flow ion mobility analysis possible. In a cross-flow ion mobility analyzer (CIMA), a component of gas flow that opposes an electric field is established within a channel. Ions are carried through the channel, and ions of a specific ion mobility are trapped by the opposing electric field and flow field and are detected when the ions reach the end of the channel. A detector at the end of the channel sees a continuous stream of ion mobility-selected ions. Different ions are selected by modifying the electric field and/or the velocity of the flow field.

It was stated previously that the single device 10 may only require slight modifications to enable other modes of operation. In the case of CIMA, the center cylindrical rod 12 could be replaced with a hollow cylinder with perforations along the length thereof to enable creation of the desired gas flow.

Figure 3:
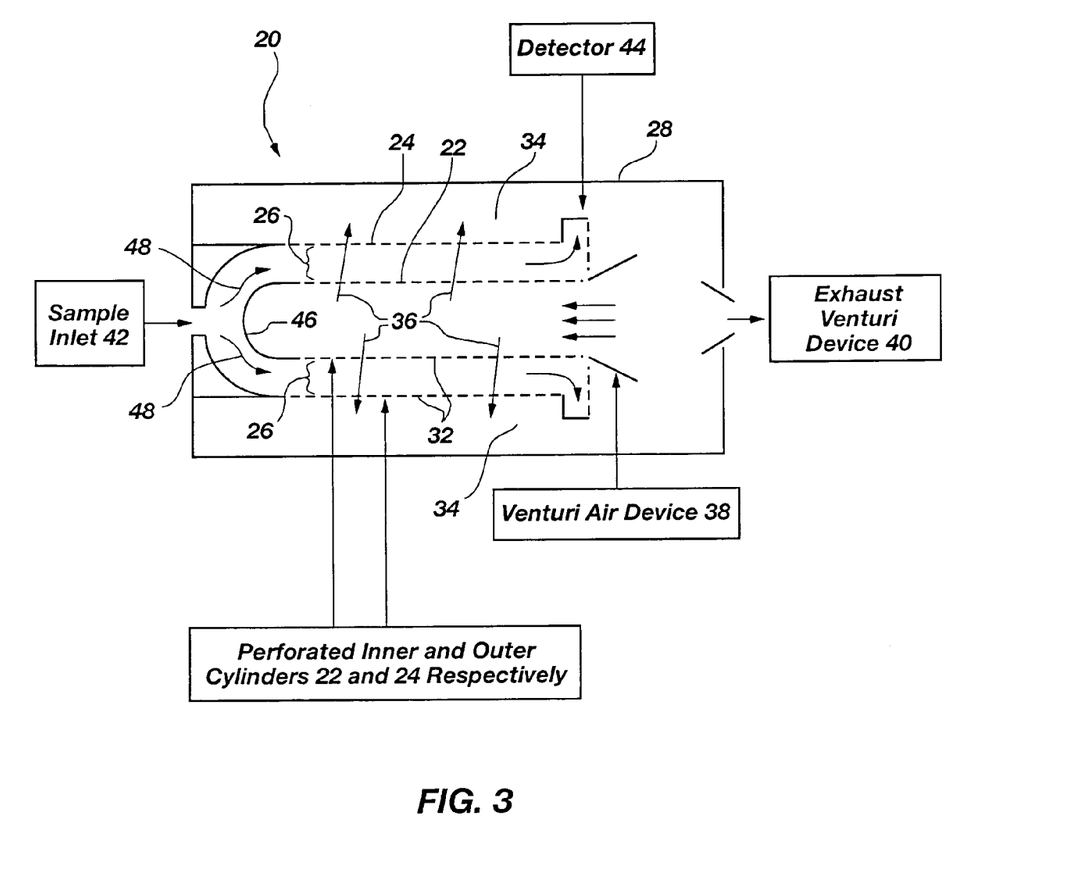
FIG. 3 is a cross-sectional profile view of a device that can perform cross-flow mobility analysis as well as operate in FAIMS and ion-mobility modes.

FIG. 3 is provided as a cross-sectional profile view of a system that can perform cross-flow ion mobility analysis. FIG. 3 shows a drift region (i.e. a cross-flow region) that is formed by the gap or space 26 between two concentric metal cylinders 22, 24. The single device 20 would now be housed in an enclosure or housing 28 that is sealed to thereby maintain the appropriate pressure and constant gas flow that is needed for operation of the single device 20 in a CIMA mode of operation.

During operation in a CIMA mode, the housing 28 is first purged of air and bathed in nitrogen gas. Both the inner and outer cylinders 22, 24 are coupled to at least two voltage sources (if ground is considered a voltage source) (not shown) so that both cylinders 22, 24 function as electrodes. The cylinders 22, 24 are set at different potentials to thereby generate a potential between the first cylinder 22 and the second cylinder 24. For additional information regarding CIMA as taught by the present invention, this application incorporates by reference all of the subject matter of U.S. non-provisional patent application Ser. No. 10/821,660 filed on Apr. 9, 2004.

In the example configuration shown in FIG. 3, the desired range for electrical potentials will generally vary from hundreds up to thousands of volts. However, it should be remembered that for whatever size of electric field that is established between the cylinders 22, 24, there will be an opposing gas flow that must be sufficiently strong enough to create a balancing effect. Nevertheless, it is possible to increase or decrease the electrical potential and the opposing fluid flow depending upon the desired performance of the present invention.

Along with the electric field that is established in a cross-flow region 30 between the cylinders 22, 24, a critical aspect of the CIMA mode is the creation of a cross-flow of gas that opposes the electric field. A velocity of the gas cross-flow is therefore set to any appropriate value as known to those skilled in the art. The gas cross-flow is shown in FIG. 3 as being created by a flow of a gas into the first cylinder 22 that is directed outwards through the holes 32 into the cross-flow region 30, and then through the holes 32 in the second cylinder 24 into a space 34 in the housing 28. This gas cross-flow is represented by lines 36. FIG. 3 indicates that a venturi air device 38 directs the gas cross-flow into the first cylinder 22. An exhaust aperture 40 is also shown in the housing 28. The figure shows a sample inlet aperture 42, a detector 44, an endcap 46, and the path 48 of ions through between the cylinders 22, 24.

Figure 4:
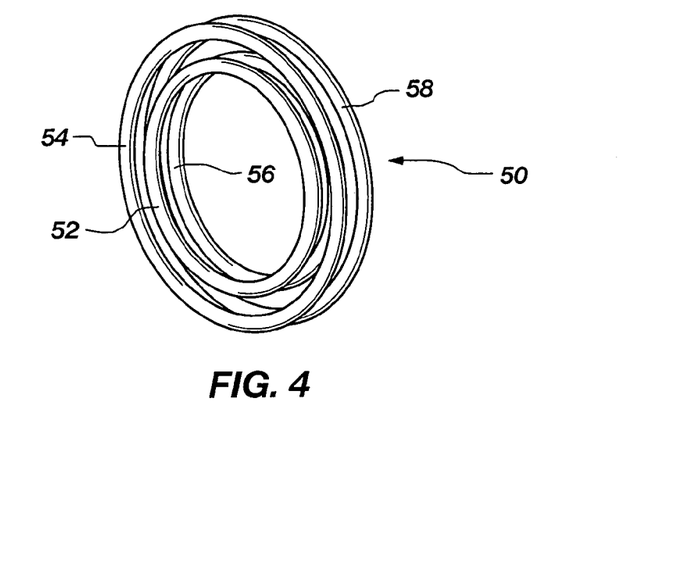
FIG. 4 is a perspective view of a storage ring ion trap.

FIG. 4 is a perspective view of a storage ring ion trap 50. The ring ion trap 50 is essentially comprised of a grouping of four coaxially aligned circular rods, wherein a first circular rod 52 is disposed coplanar with and inside a diameter of a second circular rod 54, and wherein a third circular rod 56 is disposed coplanar with and inside a diameter of a fourth circular rod 56. The first 52 and second 54 circular rods are parallel to the third 56 and fourth 58 circular rods.

Figure 5:
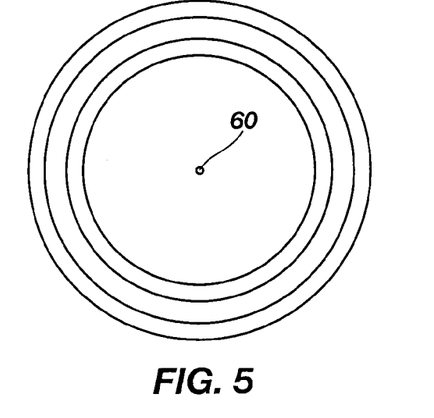
FIG. 5 is a profile view of the storage ring ion trap shown in FIG. 4.

FIG. 5 is a profile view of the storage ring ion trap 50 shown in FIG. 4.

Figure 6:
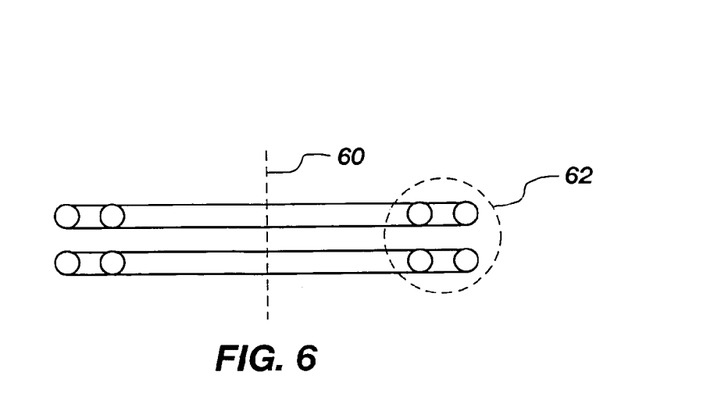
FIG. 6 is a cross-sectional view of the storage ring ion trap of FIG. 4.

FIG. 6 is a cross-sectional view of the storage ring ion trap 50 of FIG. 4. Note that a cross-section of the four circular rods 52, 54, 56, 58 with respect to a common axis of rotation 60 shows that the four circular rods form the corners of a square as denoted by dotted lines 62. It is noted that the four circular rods are not restricted to be the corners of a square, but can be any appropriate shape as known to those skilled in the art. For example, consider rods that are not of the same diameter, or rods that are tapered, or rods that are offset to create a diamond shape when seen in a cross-sectional view.

Figure 7:
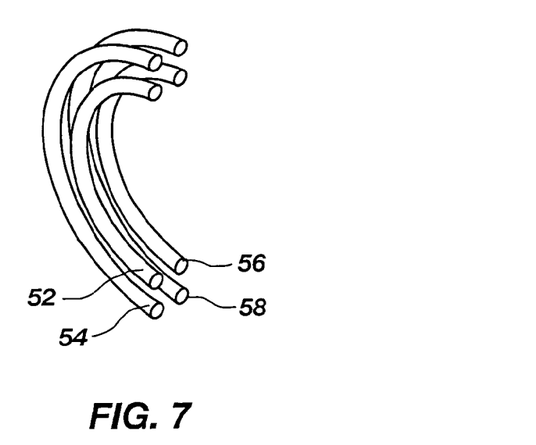
FIG. 7 is a perspective view of the cross-sectional view shown in FIG. 6.

FIG. 7 is a perspective view of the cross-sectional view shown in FIG. 6. The application of electrical potentials to these rods can be done in various ways to cause the configuration to perform as desired. For example, the two outer rods 54, 58 could have a positive electrical potential applied, while the two inner rods 52, 56 could have a negative electrical potential applied.

In contrast, the storage ring ion trap 50 would perform in a different manner if inner rod 52 and outer rod 54 were to have a positive voltage applied, and inner rod 56 and outer rod 58 were to have a negative voltage applied.

Figure 8:
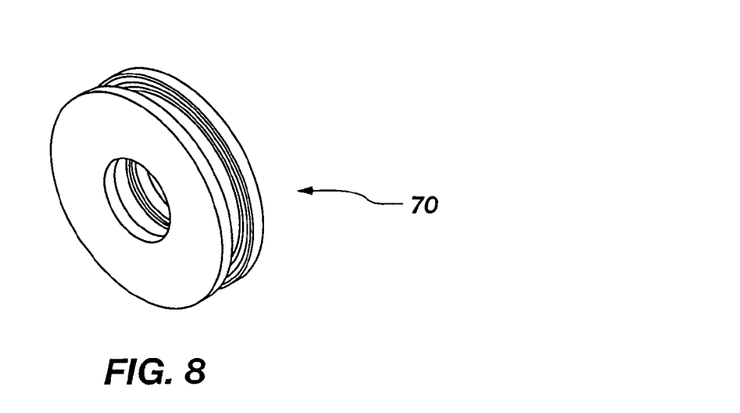
FIG. 8 is a planar open storage ring ion trap.

FIG. 8 is a perspective view of a planar open storage ring ion trap 70. It is noted that this configuration may be considered the best mode for the purposes of the present invention. In particular, various illustrations of electrical potential field lines are shown that are generated from this specific configuration of a single device for performing at least FAIMS and ITMS modes of operation.

Figure 9:
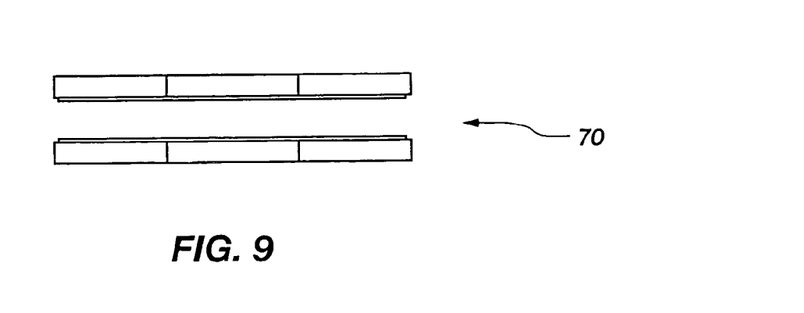
FIG. 9 is a cross-sectional view of planar open storage ring ion trap of FIG. 8.

FIG. 9 is a cross-sectional view of the planar open storage ring ion trap 70 of FIG. 8.

Figure 10:
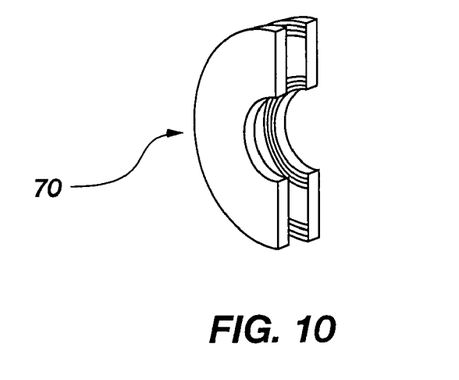
FIG. 10 is a perspective view of the cross-sectional view shown in FIG. 9.

FIG. 10 is a perspective view of the cross-sectional view of the planar open storage ring ion trap 70 shown in FIG. 9.

Figure 11:
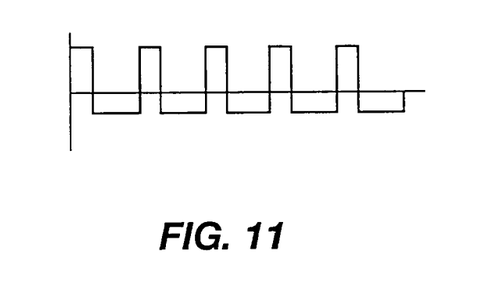
FIG. 11 is a graph of a typical FAIMS waveform.

FIG. 11 is a graph of a typical FAIMS waveform. Note that the waveform has a short high-field, and a longer low-field.

Figure 12:
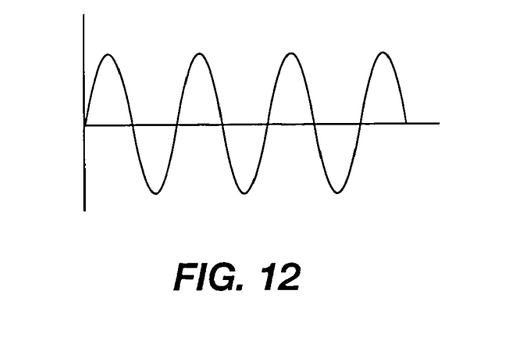
FIG. 12 is a graph of a typical applied RF field for ion mobility-based spectrometry.

FIG. 12 is a graph of a typical applied RF field for ITMS. Note that the waveform is balanced.

Figure 13:
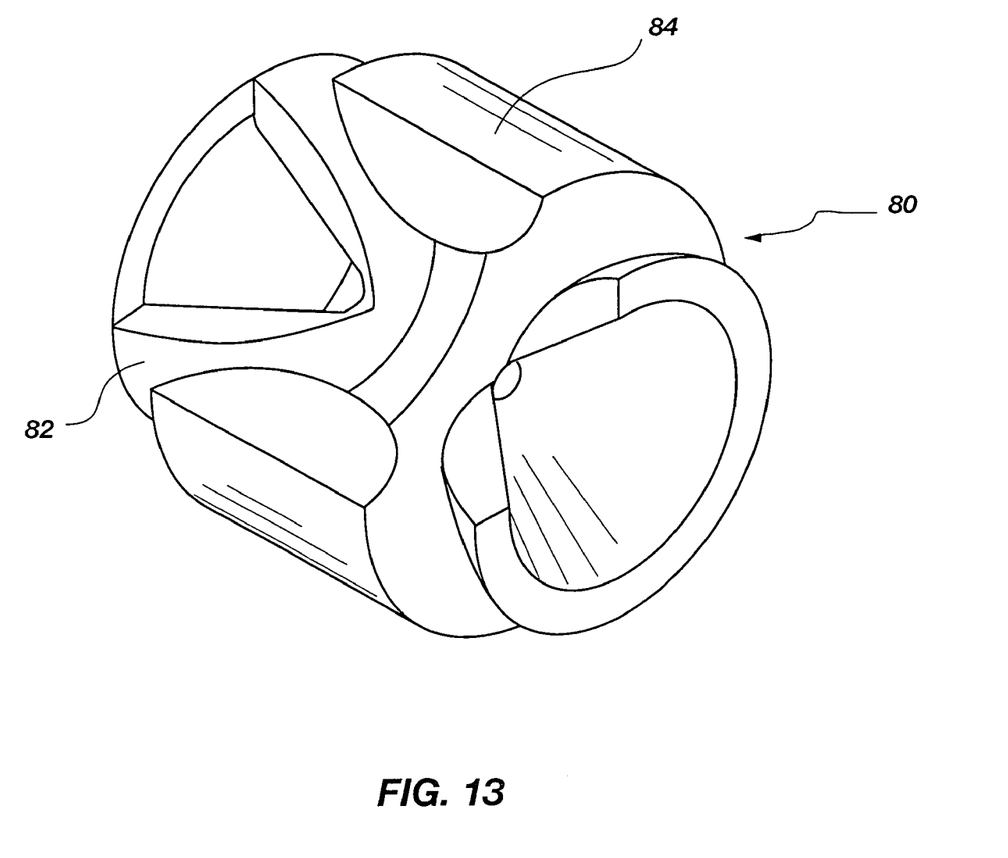
FIG. 13 is a perspective view of a conventional ion trap.

FIG. 13 is a perspective view of a conventional ion trap 80 including rings 82 and endcaps 84.

Figure 14:
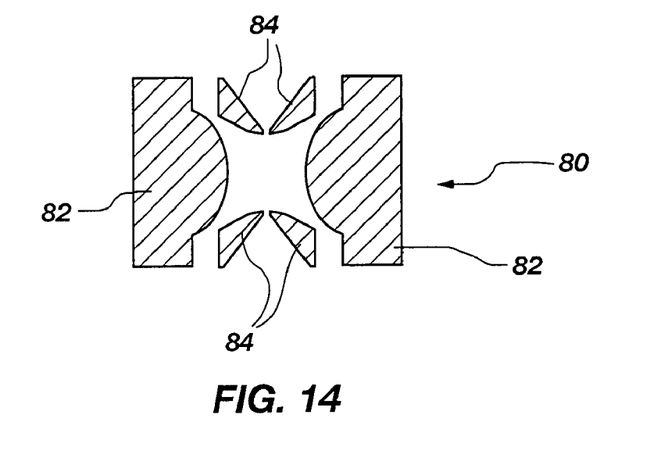
FIG. 14 is a cross-sectional view of the conventional ion trap shown in FIG. 13.

FIG. 14 is a cross-sectional perspective view of the convention ion trap 80 shown in FIG. 13. It is observed that the conventional ion trap includes rings 82, and endcaps 84.

The conventional ion trap 80 can also be used to perform FAIMS and ITMS modes of operation.

Figure 15:
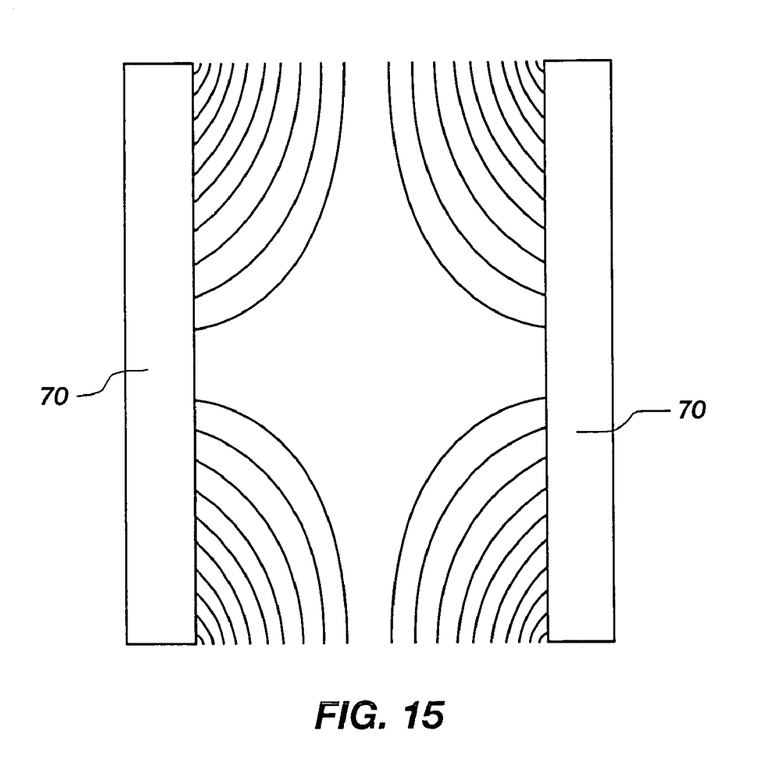
FIG. 15 is an illustration of electrical potential field lines that are present when RF is applied to the planar open storage ring ion trap of FIG. 8.

FIG. 15 is an illustration of electrical potential field lines that are present when RF is applied to the planar open storage ring ion trap 70 of FIG. 8. In order to provide a perspective to these electrical potential field lines, a cross-section of the storage ring ion trap 70 from which these electrical potential field lines are emanating is shown. This is obviously only half of the cross-sectional view.

Figure 16:
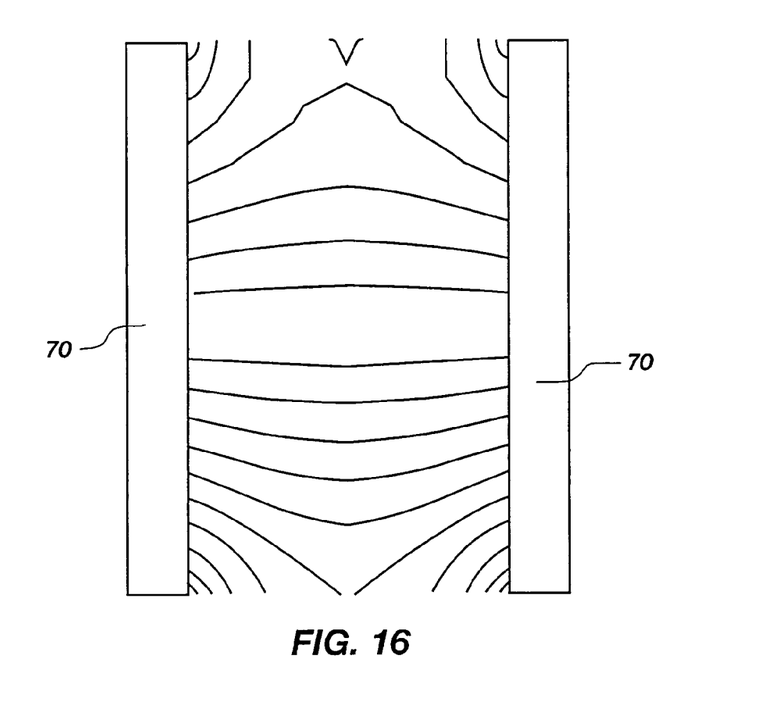
FIG. 16 is an illustration of electrical potential field lines that are present when a high field asymmetric waveform of FAIMS is applied.

FIG. 16 is an illustration of electrical potential field lines that are present when a high field asymmetric waveform of FAIMS is applied.

Figure 17:
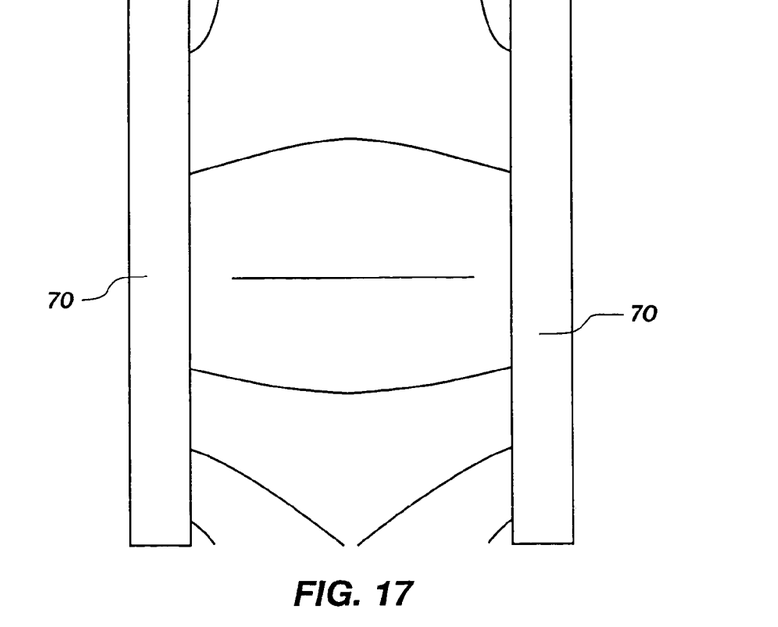
FIG. 17 is an illustration of electrical potential field lines that are present when a low field asymmetric waveform of FAIMS is applied.

FIG. 17 is an illustration of electrical potential field lines that are present when a low field asymmetric waveform of FAIMS is applied.

Figure 18:
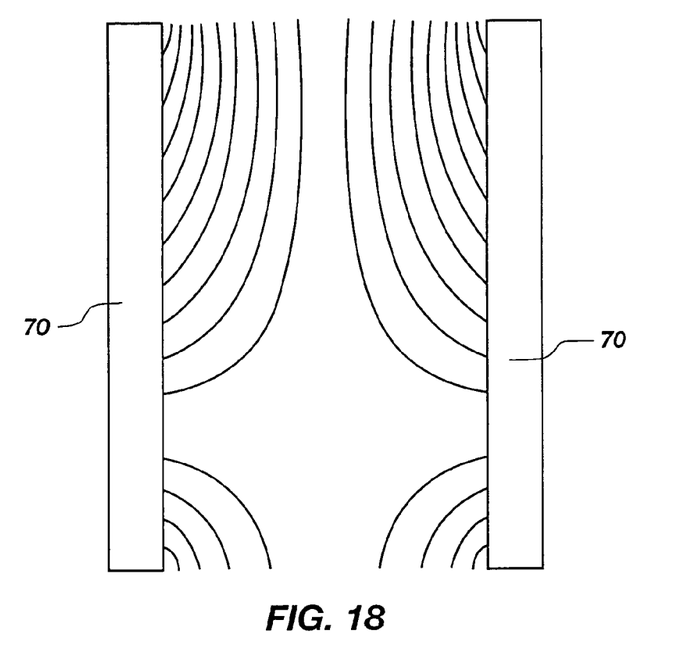
FIG. 18 is an illustration of electrical potential field lines that are present when both RF and the high field asymmetric waveform are superposed on each other.

FIG. 18 is an illustration of electrical potential field lines that are present when both RF and the high field asymmetric waveform are superposed together.

Figure 19:
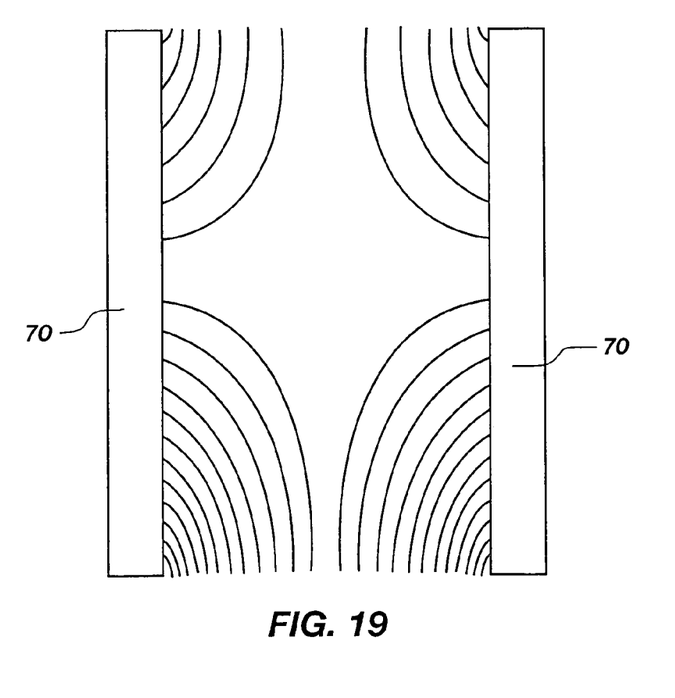
FIG. 19 is an illustration of electrical potential field lines that are present when both RF and the low field asymmetric waveform are superposed on each other.

FIG. 19 is an illustration of electrical potential field lines that are present when both RF and the low field asymmetric waveform are superposed together.

A useful concept that can be applied to the present invention is that of shimming. Shimming is the process whereby additional electrodes are strategically disposed at ends of plates, cylinders and other structures that are forming the single device of the present invention. The additional electrodes are added in order to modify electrical potential field lines. By applying electrical potentials to these additional electrodes, it is possible to substantially straighten them or make them substantially parallel to each other. This action results in improved performance of the present invention in FAIMS and ITMS modes of operation because of the affect of the field lines on the ions.

However, the affect of shimming is not confined to straightening field lines. It may be that the "idealized" field profile may have lines that are not straight or parallel. Accordingly, shimming can be performed to create a field profile that is "idealized" for any particular application, even if that application requires arcuate field lines.

There are other aspects of the present invention that have not been specifically addressed. For example, it should be understood that the present invention enables the single device to perform the various operations of FAIMS, ITMS and others. In order to perform these procedures, it may be necessary to modify the environment of the single device. For example, the pressure may need to be changed in order to perform some ion mobility-based procedure, a fragmentation procedure, and a mass spectrometry procedure. It may also be necessary to change the gas within the single device in order to perform these different procedures, or the gas may even need to be changed between operations of the same procedure. What is important is that the present invention includes the aspect of modifying the pressure and/or the gases within the single device in order to optimize the specific procedure that is to be performed.

Another aspect of the present invention is that the single device can even be created using resistive electrodes disposed on a typical circuit board. Consider a patch of resistive material that is disposed on the circuit board. An overlay forming a ring of conductive material is disposed on the resistive patch. A potential is then applied to the conductive material to thus provide a mechanically simple way to generate preferred field profiles without using discrete electrodes.

Figure 20:
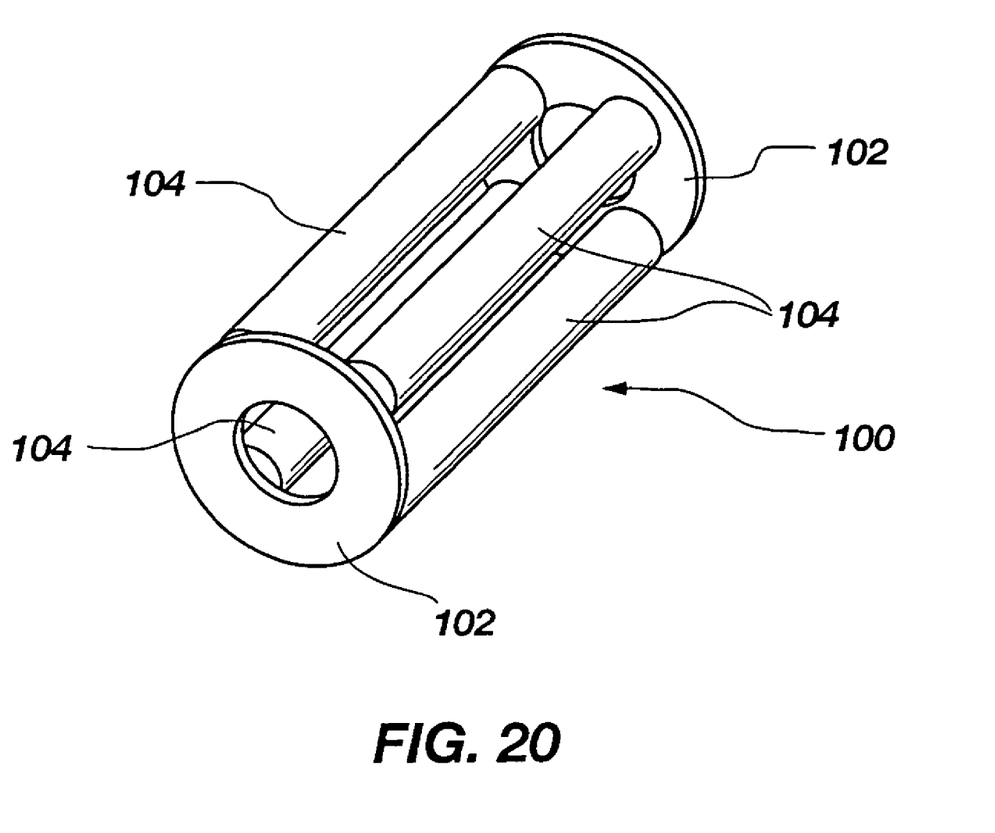
FIG. 20 is an illustration of a quadrupole that can function as the single device of the present invention.

FIG. 20 is provided as a perspective view of a quadrupole 100 that is also able to function as the single device of the present invention. However, the function of the quadrupole 100 would differ from the other devices described in this document. Specifically, performance would differ in that it may be more difficult to extract ions from within the quadrupole. However, the addition of the endcaps 102 means that it is possible to apply the RF fields to them as well as to the rods 104 of the quadrupole 100.

It should also be mentioned that separate power sources are not required for generating the FAIMS waveforms, common mode potentials, and RF potentials. Such a configuration would change the need for switches. However, it may be necessary to add systems for electronically adding or splitting electrical potentials.

It is to be understood that the above-described arrangements are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A method for using a single chamber within a separation device to separate ions according to ion mobilities and mass-to-charge ratios of charged particles and charged particles derived from atoms, molecules, particles, sub-atomic particles and ions, said method comprised of the steps of:
   1) providing an ion mobility-based and mass spectrometry system in a single chamber within a device comprised of at least two electrodes disposed so as to create an electric field therebetween, wherein the system is capable of separating ions according to ion mobilities and mass-to-charge ratios of charged particles and charged particles derived from atoms, molecules, particles, sub-atomic particles and ions within the same chamber; and
   2) operating the separation device so as to separate ions based upon ion mobility, charge, size, mass, and cross-sectional area of the ions.

2. The method as defined in claim 1 wherein the method further comprises the step of trapping the ions in the single chamber within the separation device.

3. The method as defined in claim 1 wherein the method further comprises the step of fragmenting an ion mobility selected or mass-to-charge selected ion.

4. The method as defined in claim 1 wherein the method further comprises the step of analyzing the ions that have been separated according to ion mobility, mass-to-charge, or any combination thereof.

5. The method as defined in claim 1 wherein the method further comprises the steps of:
   1) performing ion mobility-based spectrometry in the single chamber within the separation device; and
   2) performing mass spectrometry in the single chamber within the separation device.

6. The method as defined in claim 1 wherein the method further comprises the steps of:
   1) performing mass spectrometry in the single chamber within the separation device; and
   2) performing ion mobility-based spectrometry in the single chamber within the separation device.

7. The method as defined in claim 1 wherein the method further comprises the steps of performing individual procedures of ion mobility-based spectrometry and mass spectrometry in any order within the single chamber to thereby process the ions.

8. The method as defined in claim 7 wherein the method further comprises the steps of performing the procedures of ion mobility-based spectrometry and mass spectrometry any number of times but only one procedure at a time within the single chamber to thereby process the ions.

9. The method as defined in claim 8 wherein the method further comprises the step of fragmenting ions that have been selected according to mobility, mass-to-charge or any combination of mobility and mass-to-charge within the single chamber.

10. The method as defined in claim 7 wherein the method further comprises the step of performing the procedures of ion mobility-based spectrometry and mass spectrometry in a simultaneous manner within the single chamber instead of individually to thereby select a different type of ion than if the procedures were performed sequentially.

11. The method as defined in claim 1 wherein the method further comprises the step of modifying the single chamber within the separation device so that the single chamber within the separation device also has performed within it the procedure of cross-flow ion mobility spectrometry.

12. The method as defined in claim 11 wherein the method further comprises the step of performing individual procedures of ion mobility-based spectrometry, mass spectrometry, and cross-flow ion mobility spectrometry in any order within the single chamber to thereby process the ions.

13. The method as defined in claim 12 wherein the method further comprises the step of performing individual procedures of ion mobility-based spectrometry, mass spectrometry, and cross-flow ion mobility any number of times within the single chamber to thereby process the ions.

14. The method as defined in claim 1 wherein the method further comprises the steps of:
   1) providing a first electrode and a second electrode disposed so as to create an electric field therebetween;
   2) providing a first means for providing an electrical potential that is applied to the first electrode; and
   3) providing a second means for providing an electrical potential that is applied to the second electrode.

15. A system for separating ions according to ion mobilities and mass-to-charge ratios of charged particles and charged particles derived from atoms, molecules, particles, sub-atomic particles and ions within a single chamber within a separation device, said system comprised of:
   a first electrode and a second electrode disposed so as to create an electric field therebetween in the single chamber;
   a first means for providing an electrical potential that is applied to the first electrode; and
   a second means for providing an electrical potential that is applied to the second electrode.

16. The system as defined in claim 15 wherein the system is further comprised of a detector.

17. The system as defined in claim 16 wherein the first and the second electrodes are selected from the group of electrodes disposed within the single chamber and comprised of at least two concentric cylinders, at least two concentric spheres, a plurality of stacked plates, at least two substantially parallel plates, at least two substantially non-parallel plates, a plurality of straight rods, a plurality of arcuate rods, a plurality of resistive electrodes, a plurality of arcuate electrodes, and a center rod within a concentric cylinder.

18. The system as defined in claim 16 wherein the electrodes are comprised of a grouping of four coaxially aligned circular rods, wherein a first circular rod is disposed coplanar with and inside a diameter of a second circular rod, wherein a third circular rod is disposed coplanar with and inside a diameter of a fourth circular rod, wherein the first and second circular rods are parallel to the third and fourth circular rods, and wherein a cross-section of the four circular rods with respect to a common axis of rotation shows that the four circular rods form the corners of a four sided structure.

19. The system as defined in claim 17 wherein the at least two concentric cylinders are further comprised of a first cylinder and a second cylinder.

20. The system as defined in claim 19 wherein the detector is disposed at a first end of the first cylinder and the second cylinder.

21. The system as defined in claim 16 wherein the detector is selected from the group of detectors comprised of a Faraday detector, an electron multiplier, a multi-channel plate, a mass spectrometer, an ion mobility analyzer, an array detector, an image current detector, the electrodes themselves, a charge-coupled detector, a photon generating detector, and an ion-to-photon conversion device.

22. The system as defined in claim 16 wherein the system is further comprised of an ion source, wherein the ion source is disposed adjacent to an inlet aperture for delivery of ions to the single chamber.

23. The system as defined in claim 15 wherein the system is further comprised of means for analyzing ions, wherein the means for analyzing includes the ability to enable the system to only select at least one type of ion of a specific ion mobility.

24. The system as defined in claim 15 wherein the system is further comprised of means for analyzing ions, wherein the means for analyzing includes the ability to enable the system to only select at least one type of ion of a specific mass-to-charge ratio.

25. The system as defined in claim 24 wherein the system is further comprised of means for measuring ions, wherein the means for measuring includes the ability to scan through a range of ion mobilities.

26. The system as defined in claim 24 wherein the system is further comprised of means for measuring ions, wherein the means for measuring includes the ability to scan through a range of ion mass-to-charge ratios.

27. The system as defined in claim 15 wherein the first means for providing an electrical potential further comprises means for generating a high-field asymmetric waveform and the second means for providing an electrical potential comprises means for generating a different potential when operating as an ion mobility-based spectrometer.

28. The system as defined in claim 27 wherein the waveform can be varied continuously or stepwise to thereby select any specific ions of interest.

29. The system as defined in claim 27 wherein the first means for providing an electrical potential further comprises means for generating a constant potential and the second means for providing an electrical potential comprises means for generating a symmetrical waveform when operating as a mass spectrometer.

30. The system as defined in claim 29 wherein the waveform can be varied continuously or stepwise to thereby select any specific ions of interest.

31. The system as defined in claim 29 wherein the system further comprises means for simultaneously generating the electrical potentials to perform the ion mobility-based procedure and to perform the mass spectrometer procedure at the same time and within the single chamber.

32. The system as defined in claim 15 wherein the system further comprises means for exchanging a gas within the system, wherein a gas within the system is optimized for a procedure to be performed within the single chamber.

33. The system as defined in claim 15 wherein the system further comprises means for removing a gas from the single chamber.

34. The system as defined in claim 15 wherein the system further comprises means for adding a gas to the single chamber.

35. The system as defined in claim 15 wherein the system further comprises means for dynamically varying the pressure within the single chamber, to thereby optimize pressure within the system for the procedure to be performed.

36. The system as defined in claim 15 wherein the system further comprises a third electrode and a fourth electrode, wherein the first, second, third and fourth electrodes are disposed so as to form a linear quadrupole.

37. The system as defined in claim 20 wherein another detector is disposed at a second end of the first cylinder and the second cylinder.

38. The system as defined in claim 15 wherein the system is further comprised of a resistive patch disposed on a substrate, wherein the first electrode and the second electrode are disposed on the resistive patch to thereby form a potential field gradient.

39. A system for performing ion mobility-based and mass spectrometry procedures in a single chamber within a separation device simultaneously or sequentially, said system comprised of:
   a first electrode and a second electrode disposed so as to create an electric field therebetween;
   a first power source for applying a dynamic common mode potential to the first electrode; and
   a second power source for applying an asymmetric waveform to the second electrode when operating the system in an ion mobility-based spectrometry mode of operation.

40. The system as defined in claim 39 wherein the system is further comprised of:
   a third power source for applying an oscillating RF potential to the first electrode; and
   a fourth power source for applying a dynamic common mode potential.

* * * * *